US008632484B1

(12) United States Patent
Rodgers, Jr. et al.

(10) Patent No.: US 8,632,484 B1
(45) Date of Patent: *Jan. 21, 2014

(54) BRACE FOR ARM OR ELBOW REGION INCLUDING ANGULARLY-DISPLACED MUSCLE/TENDON ENGAGING PORTIONS

(75) Inventors: James Bowmar Rodgers, Jr., Atherton, CA (US); Maurice Arthur LeBlanc, Jr., Redwood City, CA (US); Raymond Neil Bilsey, Belmont, CA (US)

(73) Assignee: Squarehit Sports, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/118,566

(22) Filed: May 30, 2011

Related U.S. Application Data

(63) Continuation of application No. 12/313,018, filed on Nov. 13, 2008, now Pat. No. 7,951,104.

(60) Provisional application No. 60/987,405, filed on Nov. 13, 2007, provisional application No. 61/081,581, filed on Jul. 17, 2008.

(51) Int. Cl.
*A61F 5/37* (2006.01)
*A61F 13/00* (2006.01)
*A61B 19/00* (2006.01)
*A61F 5/00* (2006.01)
*A61F 13/06* (2006.01)
*A61L 15/00* (2006.01)
*G06Q 30/00* (2012.01)
*G06Q 20/00* (2012.01)

(52) U.S. Cl.
USPC ............. 602/20; 128/846; 128/869; 128/878; 128/881; 602/5; 602/6; 602/19; 602/60; 602/61; 602/62; 602/75; 705/14.4; 705/16; 707/948

(58) Field of Classification Search
USPC .......... 602/5, 6, 12, 20, 62, 75; 128/846, 869, 128/878, 881; 705/14.4, 16; 707/948
See application file for complete search history.

(56) References Cited

U.S. PATENT DOCUMENTS 802,623 A    10/1905  Camp
1,457,710 A   6/1923  Maxwell
(Continued)

FOREIGN PATENT DOCUMENTS

DE    4129675    4/1993
DE    4219698   12/1993
(Continued)

*Primary Examiner* — Patricia Bianco
*Assistant Examiner* — Brandon L Jackson
(74) *Attorney, Agent, or Firm* — DLA Piper LLP (US)

(57) ABSTRACT

Systems and methods are disclosed for providing supplemental support to the arm and/or elbow region of an individual. In one exemplary implementation, a brace for a user's arm is provided comprising a rigid element including arm-engaging portions and a strap of flexible material configured to encircle the arm. Moreover, the exemplary rigid element and strap may be further characterized in that the strap comprises an elastic nature or portion that provides a force (such as a compressive or constraining force) to the user's arm, the arm-engaging portions include muscle/tendon-engaging regions that each engage the user's arm along a leading face/edge, with various leading faces/edges corresponding to the muscle/tendon-engaging regions being positioned in relationship with each other to apply a desired pressure or force to the user's arm.

12 Claims, 16 Drawing Sheets

(56) References Cited

U.S. PATENT DOCUMENTS

| | | | |
|---|---|---|---|
| 1,727,897 A | 9/1929 | Ashmyers | |
| 3,288,468 A | 11/1966 | Raymond | |
| 3,669,105 A | 6/1972 | Castiglia | |
| 3,785,371 A | 1/1974 | Lewis | |
| 3,877,426 A | 4/1975 | Nirschl | |
| 3,888,244 A | 6/1975 | Lebold | |
| 3,970,081 A | 7/1976 | Applegate, Jr. | |
| 4,243,028 A | 1/1981 | Puyana | |
| 4,299,214 A | 11/1981 | Sweitzer | |
| 4,353,362 A | 10/1982 | DeMarco | |
| 4,441,490 A | 4/1984 | Nirschl | |
| 4,441,493 A | 4/1984 | Nirschl | |
| 4,682,776 A | 7/1987 | Mitchell | |
| 4,748,975 A | 6/1988 | Yashima | |
| 4,763,901 A | 8/1988 | Richter | |
| 4,807,607 A | 2/1989 | Roder | |
| 5,063,913 A | 11/1991 | Nyi | |
| 5,139,015 A | 8/1992 | Morneau | |
| 5,152,302 A | 10/1992 | Fareed | |
| 5,207,636 A | 5/1993 | Striano | |
| 5,285,537 A | 2/1994 | Hanks | |
| 5,295,951 A | 3/1994 | Fareed | |
| 5,372,575 A | 12/1994 | Sebastian | |
| 5,385,537 A | 1/1995 | Davini | |
| 5,624,388 A | 4/1997 | Lehr | |
| 5,642,739 A | 7/1997 | Fareed | |
| 5,792,093 A | 8/1998 | Tanaka | |
| 5,865,782 A | 2/1999 | Fareed | |
| 5,921,949 A | 7/1999 | Dray | |
| 5,944,682 A | 8/1999 | Milana-Panopoulos | |
| 6,007,508 A | 12/1999 | Reinhardt et al. | |
| 6,077,241 A | 6/2000 | Fareed | |
| 6,080,124 A | 6/2000 | Falk et al. | |
| 6,120,472 A | 9/2000 | Singer, Jr. | |
| 6,149,617 A | 11/2000 | McNally et al. | |
| 6,398,749 B1 | 6/2002 | Slautterback | |
| 6,478,760 B2 | 11/2002 | Darcey | |
| 6,711,750 B1 | 3/2004 | Yoo | |
| 6,755,800 B2 | 6/2004 | Weaver, II et al. | |
| 6,926,688 B2 | 8/2005 | Meyer | |
| 7,004,919 B2 | 2/2006 | Gaylord et al. | |
| 7,172,566 B2 | 2/2007 | Weaver et al. | |
| 7,173,161 B1 | 2/2007 | Kandt | |
| 7,229,426 B2 | 6/2007 | Weaver et al. | |
| D548,350 S | 8/2007 | Jordan et al. | |
| 7,393,334 B2 | 7/2008 | Tornai | |
| 7,527,602 B2 | 5/2009 | Weaver et al. | |
| 7,878,999 B2 | 2/2011 | McLean | |
| 8,082,183 B2 * | 12/2011 | Chowdhary et al. | 705/26.1 |
| 2002/0147422 A1 | 10/2002 | Darcey et al. | |
| 2005/0277859 A1 | 12/2005 | Carlsmith | |
| 2006/0052735 A1 | 3/2006 | Jablonka et al. | |
| 2006/0229539 A1 | 10/2006 | Toda | |
| 2006/0258965 A1 | 11/2006 | Lee et al. | |
| 2008/0228117 A1 | 9/2008 | Fareed | |

FOREIGN PATENT DOCUMENTS

| | | |
|---|---|---|
| DE | 29704518 | 5/1997 |
| DE | 19710288 | 8/1998 |
| EP | 126256 | 11/1984 |
| FR | 2596980 | 10/1987 |
| WO | WO 2006012745 | 2/2006 |

* cited by examiner

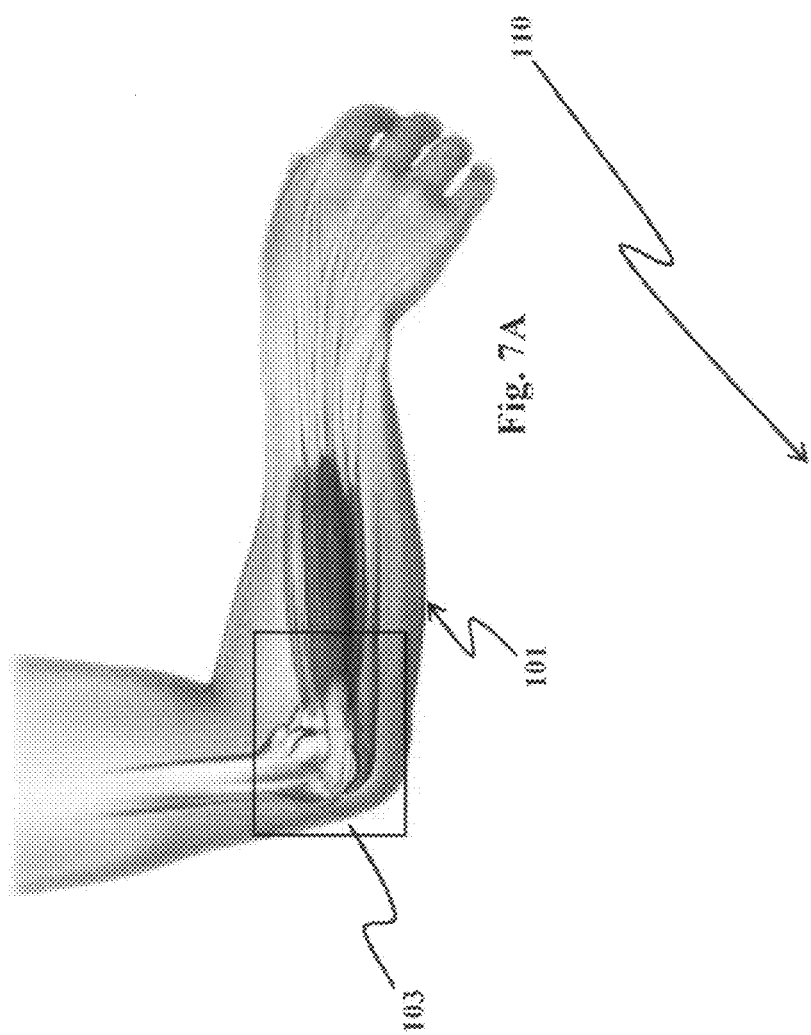

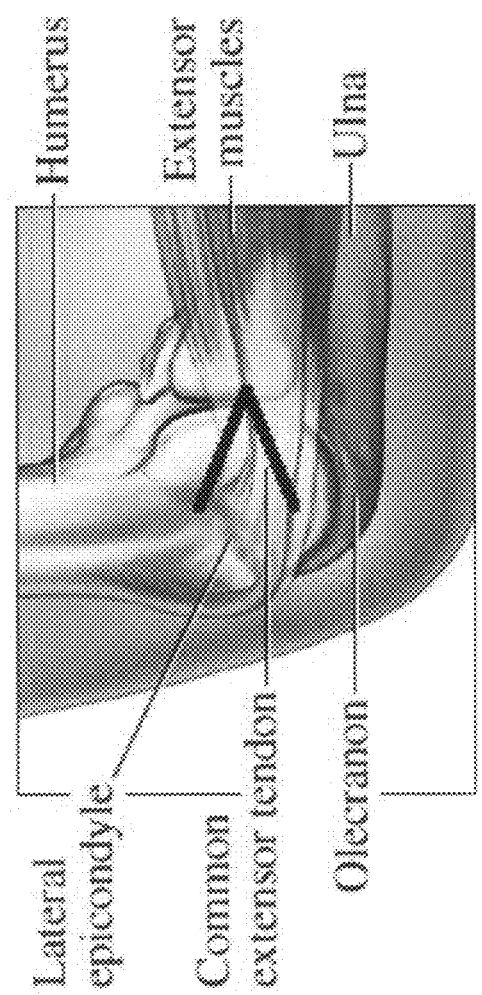

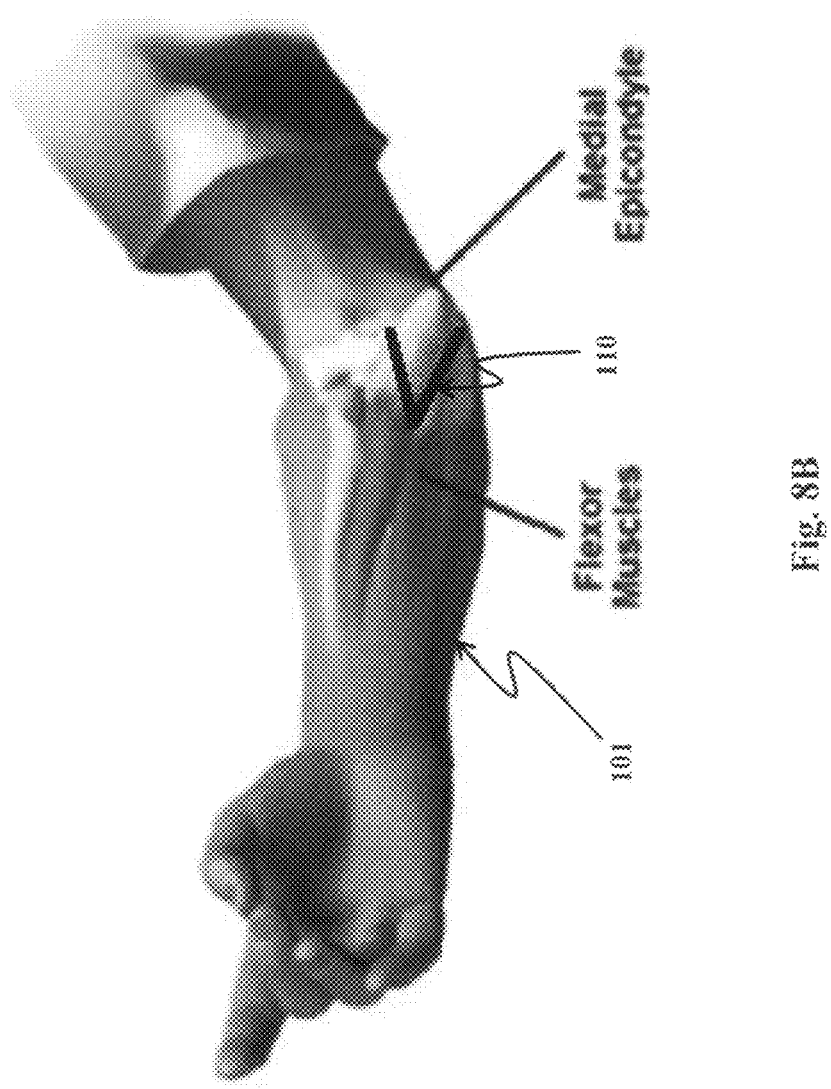

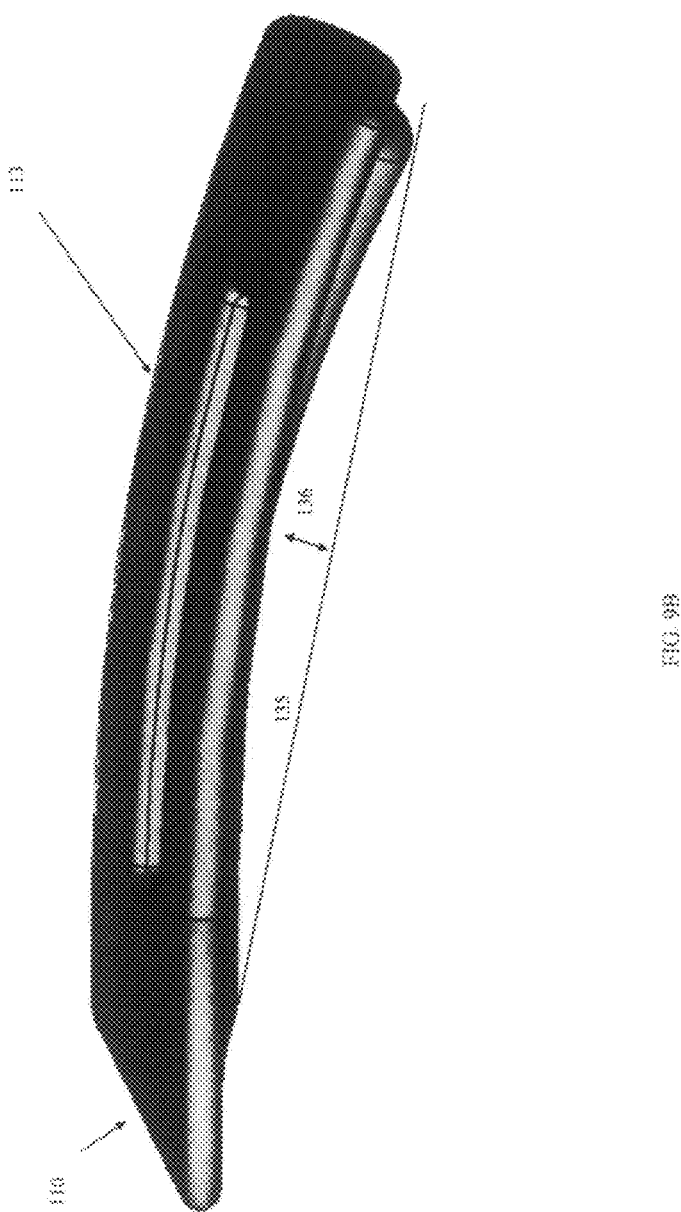

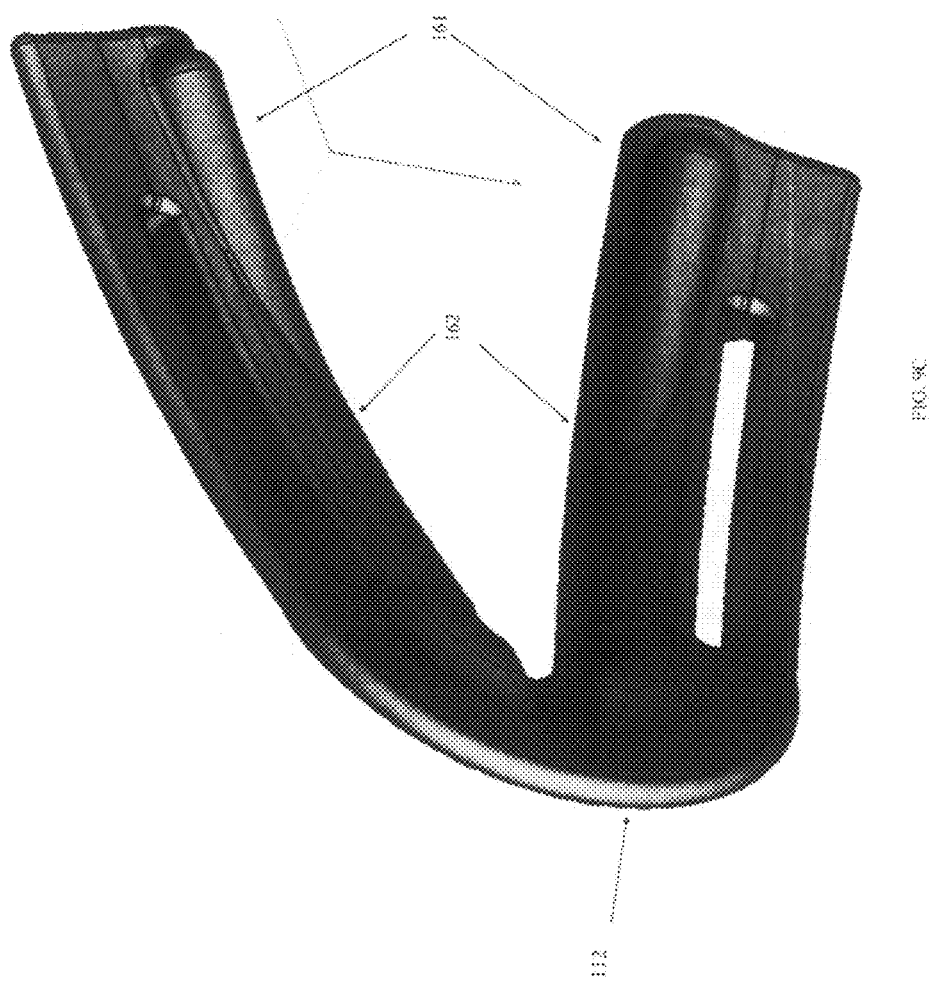

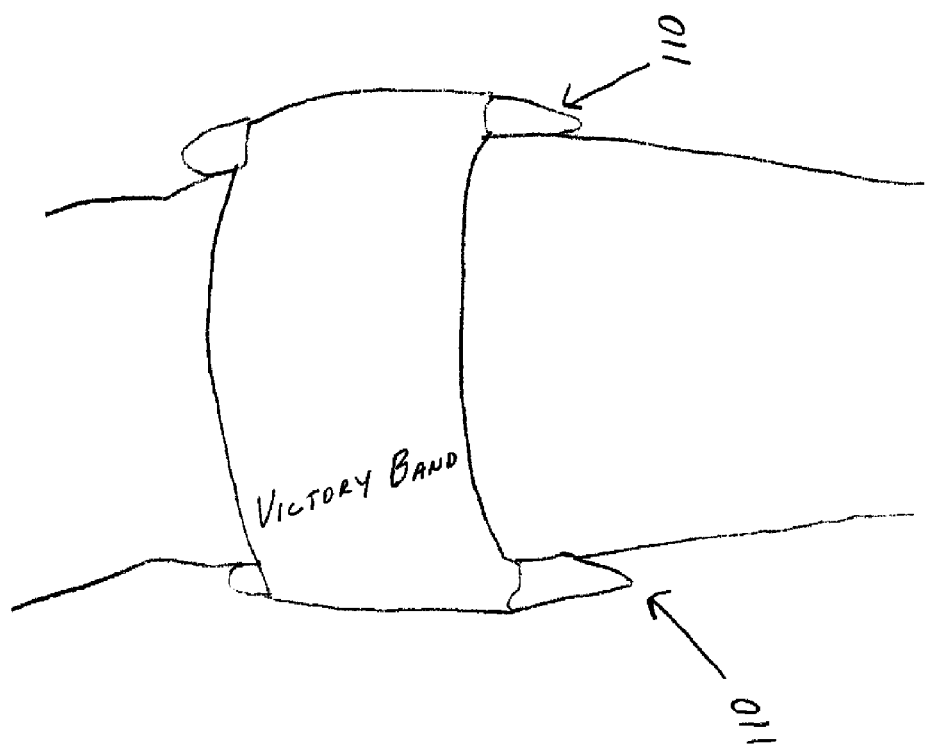

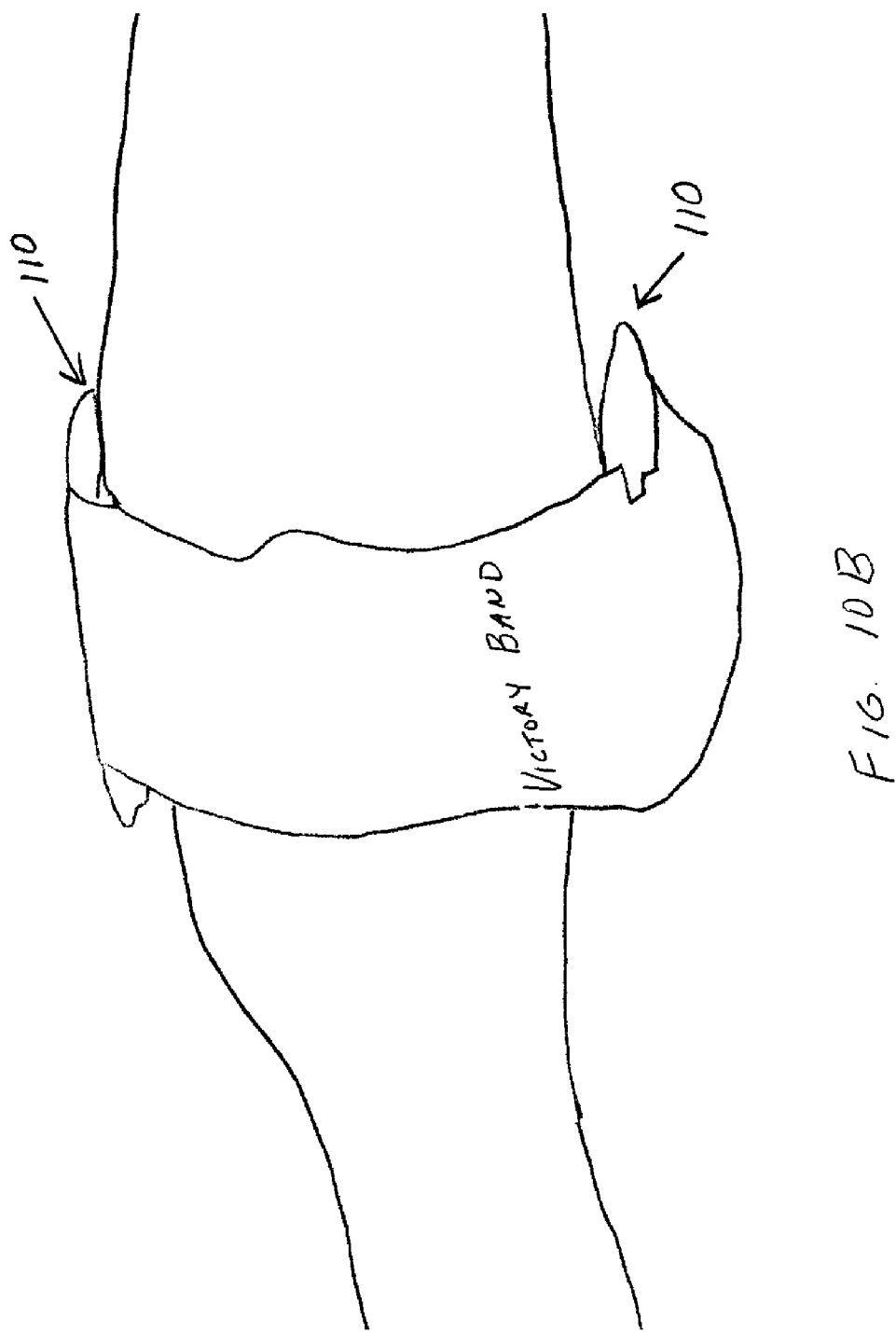

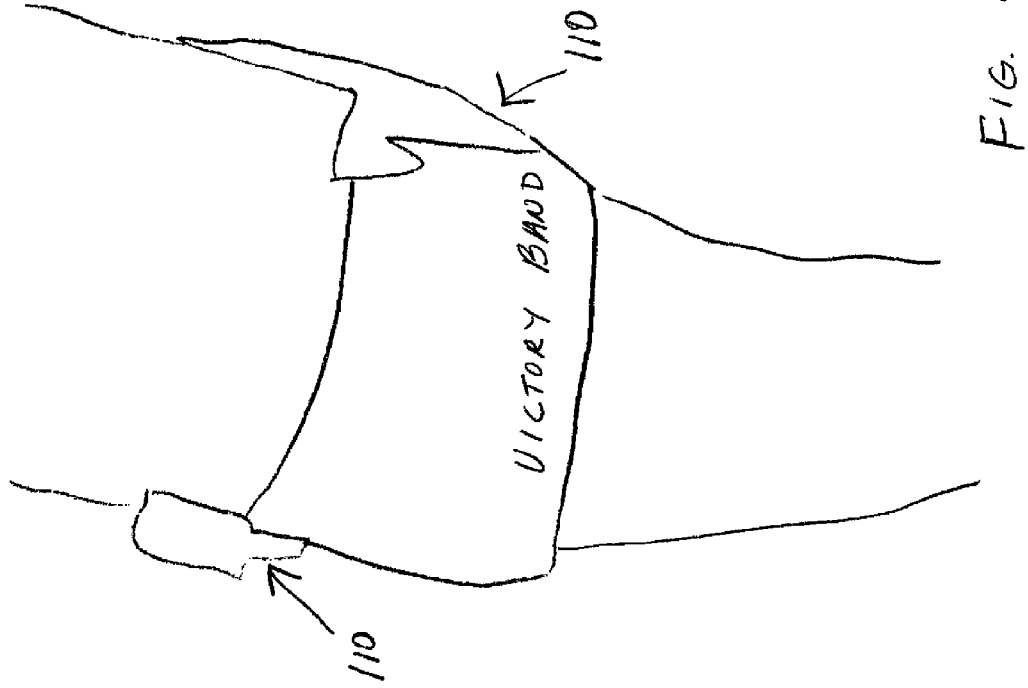

BRACE FOR ARM OR ELBOW REGION INCLUDING ANGULARLY-DISPLACED MUSCLE/TENDON ENGAGING PORTIONS

CROSS-REFERENCE(S) TO RELATED APPLICATION INFORMATION

This is a continuation of application Ser. No. 12/313,018, filed Nov. 13, 2008, published as US2009/0131842A1, now U.S. Pat. No. 7,951,104, and claims benefit/priority of provisional patent application No. 60/987,405, filed Nov. 13, 2007, and provisional patent application No. 61/081,581, filed Jul. 17, 2008, all of which are incorporated herein by reference in entirety.

BACKGROUND

1. Field

The present innovations relate to addressing and/or reducing pain caused by "tennis elbow," also referred to as "lateral/medial epicondylitis" or "epicondylagia externa," and/or to reduce the pain caused by similar/related injuries. Systems and methods consistent with the innovations herein are effective for tennis players and non-tennis players alike who suffer from such conditions.

2. Description of Related Information

Braces exist that are directed to allegedly minimizing exacerbation of various upper arm injuries, as may result from repetitive use motions in certain work- or sports-related environments, such as tennis elbow. Tennis (or golf) elbow, for example, can initially begin as a micro tear or tears often created by a non-sports related lifting motion which is then exacerbated by an over-stress or repetitive-motion from the sport or activity, sometimes, e.g., related to the attachment of the wrist extensor muscles to the lateral epicondyle.

There are numerous techniques for treating injuries characterized by a tear or tears to the extensor carpii radialus brevis. Indeed, as many as 50% of tennis players and 40% of golfers are believed to suffer from tennis elbow and/or relating tissue tear injury at some point. Further, it is believed that a large number of tennis elbow related injuries occur in people who are not tennis players or golfers, but every day working people who have repetitive movements that exacerbate the syndrome. Present techniques, however, suffer various drawbacks. Many braces, for example, apply pressure via straps that either constrict the arm in an overly rigid manner, slip, are invariably over-tightened by users, and/or are uncomfortable to wear during competitive sports activities. Some braces or bands, for example, put pressure around the entire forearm and cause the player to 'over-tighten' in an effort to apply pressure where pressure is needed.

Prevailing medical solutions include a three-step program to remedy the cause of tennis elbow is (1) first, rest and ice, (2) then gradual stretching and start of mild exercise, and (3) most importantly, a regimented routine doing the correct exercise in the correct way to strengthen and make healthy the muscles causing tennis elbow thereby eliminating attendant pain and discomfort.

Aspects of the innovations herein are intended to enable individuals to continue playing sports or engaging in physical activities, while minimizing or reducing pain and/or additional injury, as may preferably/also be done in the context of undertaking and maintaining a correct exercise and healing program.

SUMMARY

Systems and methods consistent with the innovations herein are directed to providing supplemental support to the arm and/or elbow region of an individual.

In one exemplary implementation, a brace for a user's arm is provided comprising a rigid element including arm-engaging portions and a strap of flexible material configured to encircle the arm. Moreover, the exemplary rigid element and strap may be further characterized in that the strap comprises an elastic nature or portion that provides a force (such as a compressive or constraining force) to the user's arm, the arm-engaging portions include muscle/tendon-engaging regions that each engage the user's arm along a leading face/edge, with various leading faces/edges corresponding to the muscle/tendon-engaging regions being positioned in relationship with each other to apply a desired force to a user's arm.

It is to be understood that both the foregoing general description and the following detailed description are exemplary and explanatory only and are not restrictive of the invention, as described. Further features and/or variations may be provided in addition to those set forth herein. For example, the present invention may be directed to various combinations and subcombinations of the disclosed features and/or combinations and subcombinations of several further features disclosed below in the detailed description.

DESCRIPTION OF THE DRAWINGS

The accompanying drawings, which constitute a part of this specification, illustrate various embodiments and aspects of the present invention and, together with the description, explain the principles of the invention. In the drawings:

FIGS. 7A and 7B illustrate exemplary muscle/tendon anatomy of the elbow region of a user as well as a representation of an exemplary device at an exterior forearm location consistent with certain aspects related to the innovations herein.

FIGS. 8A and 8B illustrate exemplary muscle/tendon anatomy of the elbow region of a user as well as a representation of an exemplary device at an interior forearm location consistent with certain aspects related to the innovations herein.

FIGS. 9A-9C illustrate further additional implementations and perspective views of exemplary braces consistent with certain aspects related to the innovations herein.

FIGS. 10A-10C are illustrations of another exemplary device consistent with certain aspects related to the innovations herein.

DETAILED DESCRIPTION OF EXEMPLARY IMPLEMENTATIONS

Reference will now be made in detail to the innovations herein, examples of which are illustrated in the accompanying drawings. The implementations set forth in the following description do not represent all implementations consistent with the claimed invention. Instead, they are merely some examples consistent with certain aspects related to the invention. Wherever possible, the same reference numbers will be used throughout the drawings to refer to the same or like parts.

Aspects of the innovations herein may apply localized pressure to the injured area (e.g., damaged tendon/muscle group, etc.), for example, by straddling and dampening forearm muscle movement during activity or exercise, such that, inter alia, strain on the injured tendon/muscle group is reduced and/or restricted.

Figure 1:
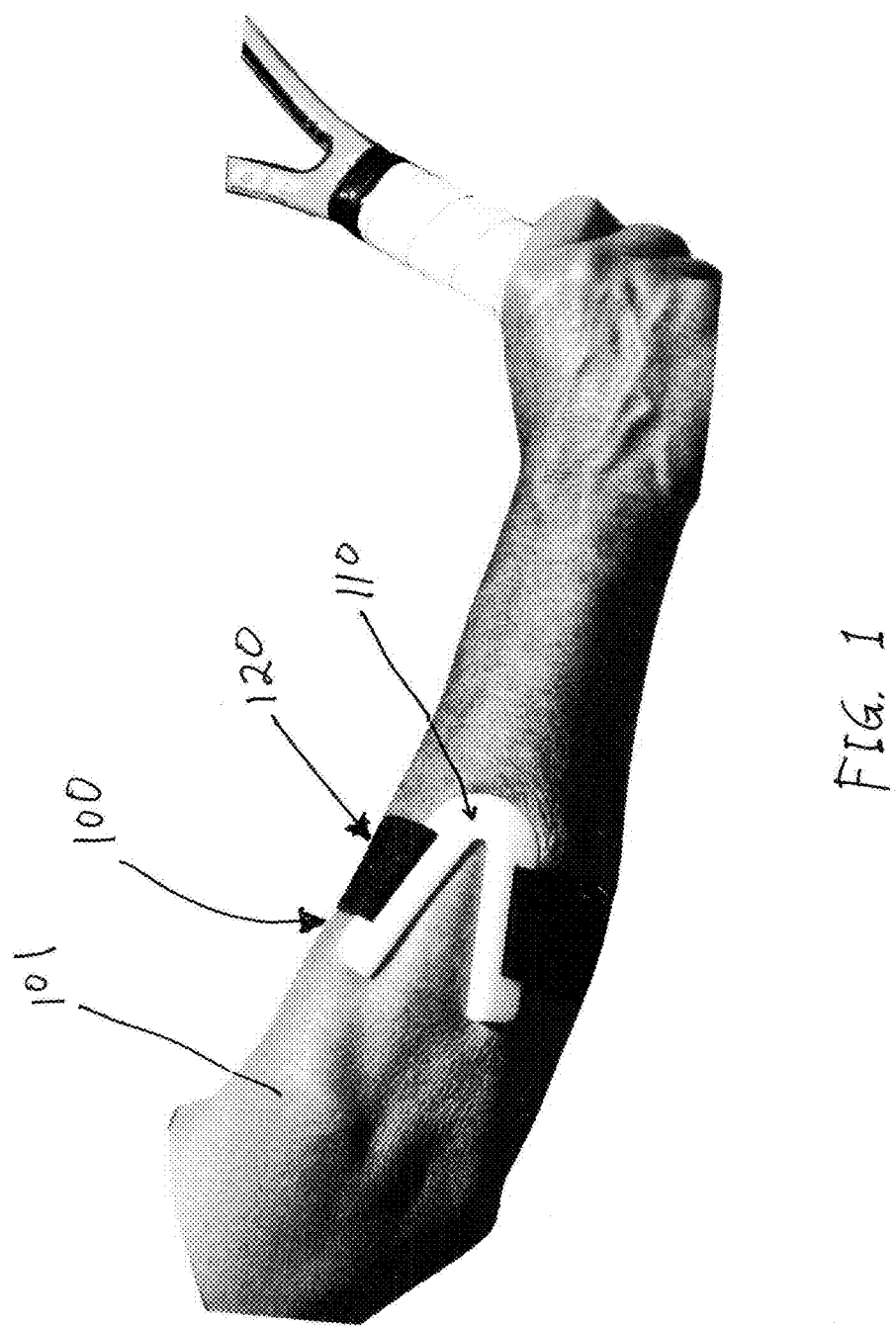
FIG. 1 illustrates an exemplary device positioned on the arm of a tennis player consistent with certain aspects related to the innovations herein.

FIG. 1 is a diagram of an exemplary brace 100 consistent with certain aspects related to the present innovations. Referring to FIG. 1, brace 100 may comprise a brace element 110 and a strap 120, which encircle a user's arm 101. According to some implementations, brace element 110 may cradle/straddle one or more muscles of the extensor/flexor muscle group and/or one or more tendons, for example, those that join at or are located near the lateral epicondyle or the medial epicondyle. Brace element 110, for example, may be a "V" shaped member, although "U"-shaped and/or other implementations may also be used so long as the pressure applied to the arm is consistent with the disclosure herein. Further, as explained in more detail below, the brace element 110 may cradle or straddles the three elbow/upper forearm tendons (see, e.g., FIG. 7B) as they join into one common tendon at the lateral epicondyle. Such implementations may also gather the injured area/tissue as it is pulled up the forearm by the brace element 110 and constrained in place, which beneficially restricts movement of the injured area(s).

In one representative implementation, for example, a brace for a user's arm may comprise a brace element 110 that includes arm-engaging portions or regions and a strap 120 of flexible material configured to encircle the user's arm and to thereby secure the brace element 110. In the exemplary brace shown in FIG. 1, the arm-engaging portions might loosely be seen as corresponding to the 2 legs of the "V" shape, although the arm-engaging portions are sometimes more aptly characterized via the surfaces or manner by which they engage the user's muscles/tendons. In other words, arm-engaging portions need not necessarily be formed in any such particular shape, or have any particular outward appearance, as in some implementations they may be best characterized by the underlying forces they apply to the user's muscles/tendons. Indeed, here, the arm-engaging portions may include muscle/tendon-engaging regions that each engage one or more muscles and/or tendons of the user's arm along a leading face/edge (not shown in FIG. 1). In some implementations, the leading face/edge may include a raised portion, rail or rib that provides even greater focus of the brace's force to the desired muscle(s)/tendon(s). In general, a first leading face/edge corresponding to a first muscle/tendon-engaging region may be positioned in an angularly displaced relationship with respect to a second leading face/edge corresponding to a second muscle/tendon-engaging region. These leading faces/edges may then act together to reduce movement of the injured area during exercise or work and stabilize the injured area/muscles/tendons, reducing or minimizing additional damage and pain. Such isolation of the affected area, for example, may relieve an injured tendon from forces of repetitive use during athletic activity, whereby the Innovations provide greater comfort to the user and decrease chances of additional injury.

Figure 2:
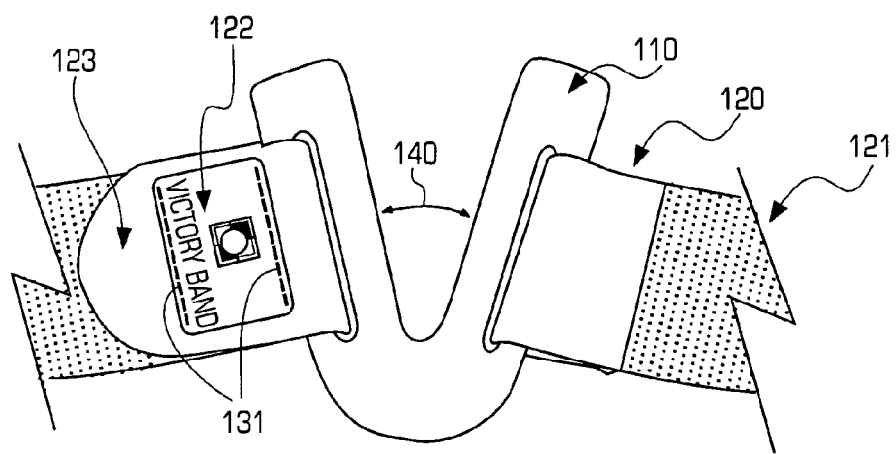
FIG. 2 illustrates a front or topside view of an exemplary device consistent with certain aspects related to the innovations herein.

FIG. 2 illustrates a front or topside view of an exemplary device consistent with certain aspects related to the innovations herein. The exemplary device depicted, here, includes the brace element 110 and the encircling strap 120, which may also include or be comprised of an elastic portion 121. Any ends of the strap 120 may also be formed to include tapered end sections, such as the rounded end section 123 shown in FIG. 2, to eliminate catching or snagging of a closure and/or inadvertent release of the brace. Further, indicia such as a logo element 122 may be incorporated into the strap, and such indicia may be stitched to the strap only along stitch lines 131 perpendicular to the length of the strap such that the flexibility and comfort of the strap is not limited by stiffness associated with indicia attachment along the longitudinal axis of the strap.

Figure 3:
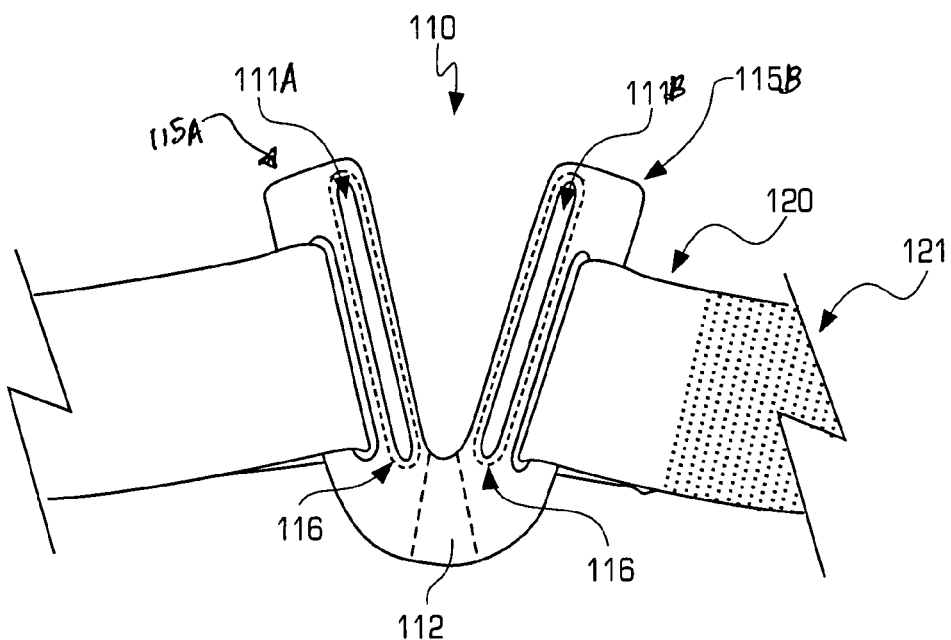
FIG. 3 illustrates a bottom view of an exemplary device consistent with certain aspects related to the innovations herein.

FIG. 3 illustrates a bottom view of an exemplary device consistent with certain aspects related to the innovations herein. Here, the underside of a brace, illustrating exemplary features facing a user's arm, is shown. Referring to FIG. 3, an exemplary brace may include the brace element 110 having arm-engaging portions 115, the encircling strap 120, which may include or be comprised of an elastic portion 121, as well as the muscle/tendon-engaging regions 116 of the brace element 110. Further, within the muscle/tendon-engaging regions, raised rails or ribs may also be included to provide more localized pressure upon the muscles/tendons of interest. Such rails or ribs may be positioned and/or angle to provide a push or force proximally to help relieve the forces on the tendon at the epicondyle. Rails or ribs may also concentrate more force, such as compressive force, onto the muscles/tendons/arm via the brace element so that there is less pressure and discomfort on the user's arm circumferentially (associated with the strap). Further, rails or ribs provide a more localized or constrictive force, such as a force that constrains a specific tendon to reduce "bouncing" and side-to-side motion and lessen the destructive pull on the tendon. A "V"-shaped brace element 110, for example, may also straddle the lateral epicondyle and form a channel around the tendon to facilitate the tendon in doing its job. Indeed, a groove 112, having a recession away from the user, may also be included to: (1) assist in positioning or centering the brace upon the proper muscle(s)/tendon(s); (2) provide for greater concentration of force via the muscle/tendon-engaging regions by eliminating the pressure point against the user's arm at that spot and enabling that force to be channeled through the remaining portions of the brace element that are in contact with the user; and (3) eliminate a pressure point otherwise caused by that portion cutting into the muscle or tendon directly beneath. This groove may also be used as a pain locator nexus, which enables the brace element to be easily positioned or adjusted over a point of greatest pain to best reduce a user's specific pain symptom(s).

In another representative implementation, which more closely corresponds to the exemplary brace shown in FIGS. 1-3, a brace may comprise a brace element 110 that includes 2 arm-engaging portions 115 as well as a strap 120 of flexible material attachable to the brace element 110 and configured to encircle the arm. The arm-engaging portions 115 may include muscle/tendon-engaging regions 116 that each engage one or more muscles and/or tendons of the user's arm along a leading face/edge 111. As explained above, leading faces/edges may be further augmented in some implementations via raised portions, rails or ribs to further concentrate the force being applied to the particular muscle(s)/tendon(s) of interest. Turning back to the illustrated implementation, a first leading face/edge 111A corresponding to a first muscle/tendon-engaging region 116A is positioned in an angularly displaced relationship (here, given by an acute angle 140) with a second leading face/edge 111B corresponding to a second muscle/tendon-engaging region 116B. Further, in a broad implementation, the first leading face/edge 111A may be angularly displaced at an angle 140 between about 15 degrees and about 85 degrees from the second leading face/edge 111B. Moreover, in other implementations, the first leading face/edge may be angularly displaced from the second leading face/edge is one of several desired ranges, including but not limited to between about 20 degrees and about 65 degrees, between about 22 degrees and about 45 degrees, between about 24 degrees and about 40 degrees, between about 26 degrees and about 35 degrees, as well as at about 30 degrees, at about 31 degrees, and at about 32 degrees. Such angular relationship can constitute a "V" shape that gathers the tendons as they emerge from the muscles, in the region where their shape starts to narrow down from the muscle bulge. These innovations, as well as implementations consistent therewith such as "U"-shaped arrangements, act to contain the muscle(s) or tendon(s), rather than just pressing down on them as with existing devices. Such angular relationships are particularly advantageous when used to treat lateral epicondylitis or "tennis elbow," as they isolate the common extensor tendon from repetitive motion stress.

Further, aspects of the systems and methods herein may isolate the injured soft tissue by allowing the muscle/tendon-engaging, "V" or "U" shaped, etc regions in the device to encompass and cradle the painful area and apply downward pressure, which may also serve to "short circuit" associated pain. Undesired wrist flexion movement may also be limited. Moreover, because of both the reduction in pain to a user and the minimization of additional tearing or injury, devices consistent with the innovations herein allow individuals to continue playing desired sports such as tennis, golf, etc. or to otherwise continue engaging in important physical activities. In certain implementation, such as with the "V" shape, the device tends to push proximally to help relieve the forces on the tendon at the epicondyle. (This feature can be accentuated by putting vertical/downward force on top legs of the "V" and an upward or proximal force at the apex of the "V.")

Figure 4:
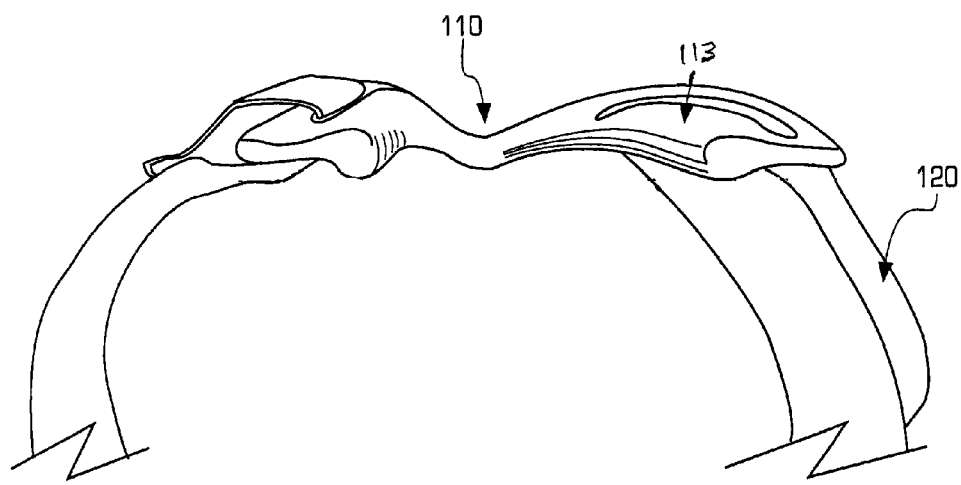
FIG. 4 illustrates a side view perspective of an exemplary device consistent with certain aspects related to the innovations herein.

FIG. 4 illustrates a side view perspective of an exemplary device consistent with certain aspects related to the innovations herein. FIG. 4 shows the side edge of an exemplary device showing the brace element 110, an encircling strap 120, as well as the curvature of the legs of one exemplary "V"-shaped implementation consistent with certain aspects related to the innovations herein. As with other implementations, the brace member 110 may be molded nylon, plastic or other suitable rigid or semi-rigid material. Regarding curvature, as also seen in connection with FIG. 9B, aspects of the innovations herein also include computer-assisted design enabling the brace to best apply its force against the rounded shape and muscles/tendons of the forearm. The radial shapes of the brace, specified herein, allow it to conform to the arm and injured area more properly, effecting some of the advantages set forth herein. For example, the brace element 110 may have a first or side curvature, as measured along a side view perspective (i.e., as seen here in FIG. 4), characterized within one of three ranges: first, having a rise or height 136 (see FIG. 9B) of about 1 mm to about 8 mm, along a run (length) 135 of about 5 to about 9 cm; second, having a rise (height) 136 of about 2 mm to about 6 mm, along a run (length) 135 of about 6 to about 8 cm; and/or third, having a rise 136 of about 3 mm to about 4 mm, along a run (length) 135 of about 7 cm. This curvature, in connection with features such as straps with suitable elasticity and having a brace element of sufficient thickness and/or additional muscle/tendon-engaging elements such as raised portions, rails or ribs, enables the brace to provide a greater concentration of force downward onto the desired muscle/tendon groups. Further, certain innovations may also include a curvature as seen from a top side view perspective (see, e.g., FIG. 5), which may even further augment the concentration of force and advantages set forth herein.

Figure 5:
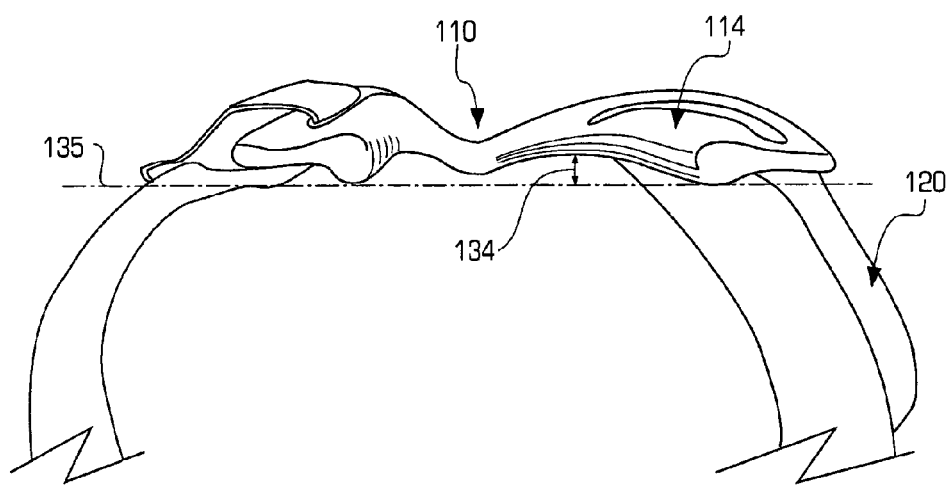
FIG. 5 illustrates a top side view perspective of an exemplary device consistent with certain aspects related to the innovations herein.

FIG. 5 illustrates a top side view perspective of an exemplary device consistent with certain aspects related to the innovations herein. As shown in FIG. 5, an exemplary brace may include the brace element 110, the encircling strap 120, and the top curvature of the legs 113 of the brace element 110 (shown in this example, with the "V" shape). As mentioned above, this top side view curvature may be implemented in conjunction with FIG. 4's side view curvature, although it may of course be implemented on it own. Here, for example, the brace element 110 may have a second or top side curvature, as measured along a top side view perspective (i.e., as seen here in FIG. 5), characterized within one of three ranges: first, having a rise 134 of between about 1 mm and about 6 mm along a run (length) 135 of about 2 to about 6 cm; second, having a rise (height) 134 of about 2 mm to about 5 mm, along a run (length) 135 of about 3 to about 5 cm; and/or third, having a rise (height) of about 3 mm to about 4 mm, along a run (length) of about 4 cm. The effects and advantages of this curvature are consistent with those of the pure side curvature discussed above in connection with FIGS. 4 and 9B.

Figure 6:
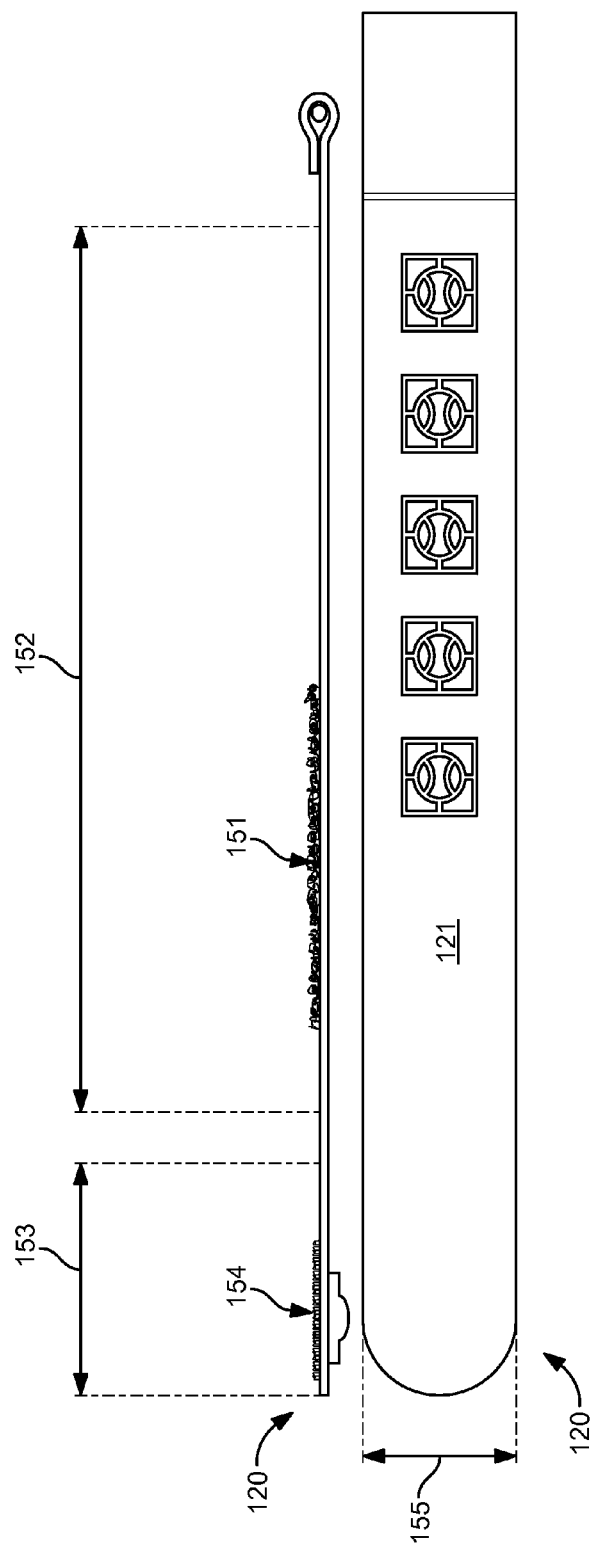
FIG. 6 illustrates side and top views of an exemplary strap consistent with certain aspects related to the innovations herein.

FIG. 6 illustrates side and top views of an exemplary strap consistent with certain aspects related to the innovations herein. As shown in FIG. 6, the strap may be of elastic nature or include or be comprised of an elastic portion 121 that provides, via exertion by the arm-engaging element, a force or compressive/constraining force to the user's arm. Further, the strap may also include first hook-and-loop material 151 on the exterior of a first portion 152 of the strap encircling the user's arm and a second portion of the strap used to affix the rigid element, wherein the second portion of the strap includes an end region 153, which has complementary hook-and-loop material 154, that attaches to the first hook-and-loop material to secure the rigid element. As such, the forces applies to a user's arm by the brace member are adjustable with tensioning of the straps, and "numbness" often associated with stiff strap arm bands is eliminated or significantly reduced. Additionally, the end 153 of the strap used to secure the brace may include a pad, such as a tacky rubber pad, for ease of grasping the band closure and adjusting the brace easily. Moreover, this pad may also include a logo or other indicia to draw observers attention to the subject matter printed thereon.

FIGS. 7A and 7B illustrate exemplary muscle/tendon anatomy of the elbow region of a user as well as a representation of an exemplary device at an exterior forearm location consistent with certain aspects related to the innovations herein. A region 103 of a user's forearm 101 in FIG. 7A is shown expanded in FIG. 7B. FIG. 7B illustrates one exemplary placement of a brace consistent with the innovations herein, at the location where the wrist extensor tendons attach to the lateral epicondyle. Via such strategic placements, the innovations herein reduce movement of the injured area during play or work and stabilizes the injured area/tendons, minimizing or reducing additional damage and pain. As such, the innovations herein can be employed to minimize further injury, especially in conjunction with an overall healing regimen.

Figure 8A:
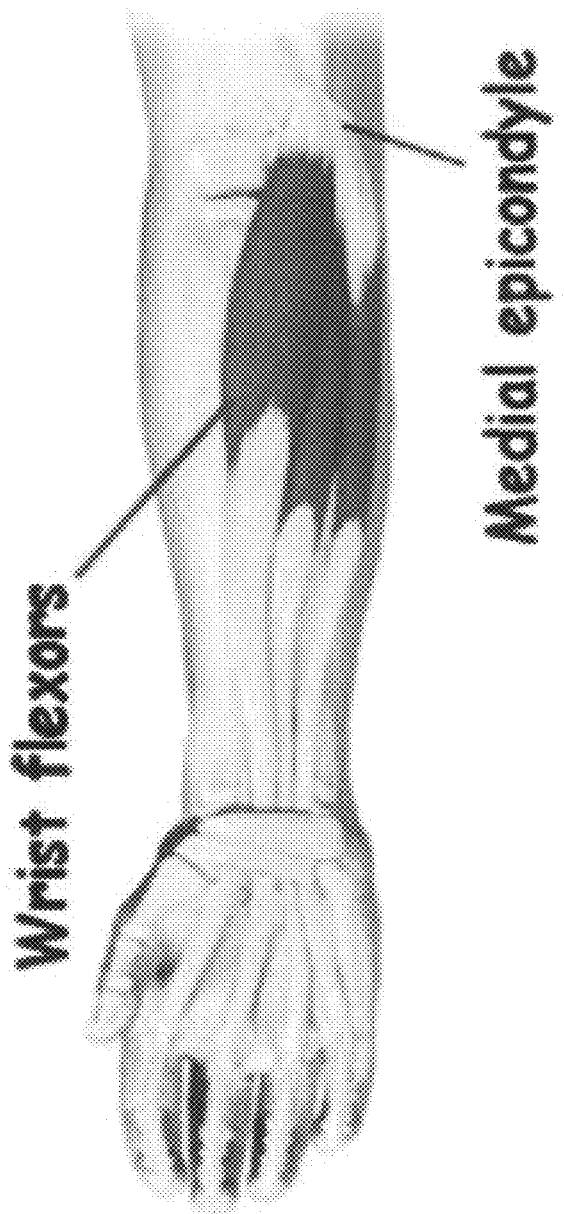

FIGS. 8A and 8B illustrate exemplary muscle/tendon anatomy of the elbow region of a user as well as a representation of an exemplary device at an interior forearm location consistent with certain aspects related to the innovations herein. FIG. 8A is a diagram illustrating the anatomy of the interior a user's forearm 101, including wrist flexor muscles and the medial epicondyle. FIG. 8B is a diagram illustrating a close-up of the elbow showing placement of the brace element 110 (here, "V"-shaped for purposes of illustration) at the location where the wrist flexor tendons attach to the medial epicondyle. Such placement is beneficial in reducing further tears to these interior muscles/tendons and imparts effects and advantages regarding injuries to this region of the arm consistent with those set forth in connection with the exterior arm muscle/tendon groups described above.

Figure 9A:
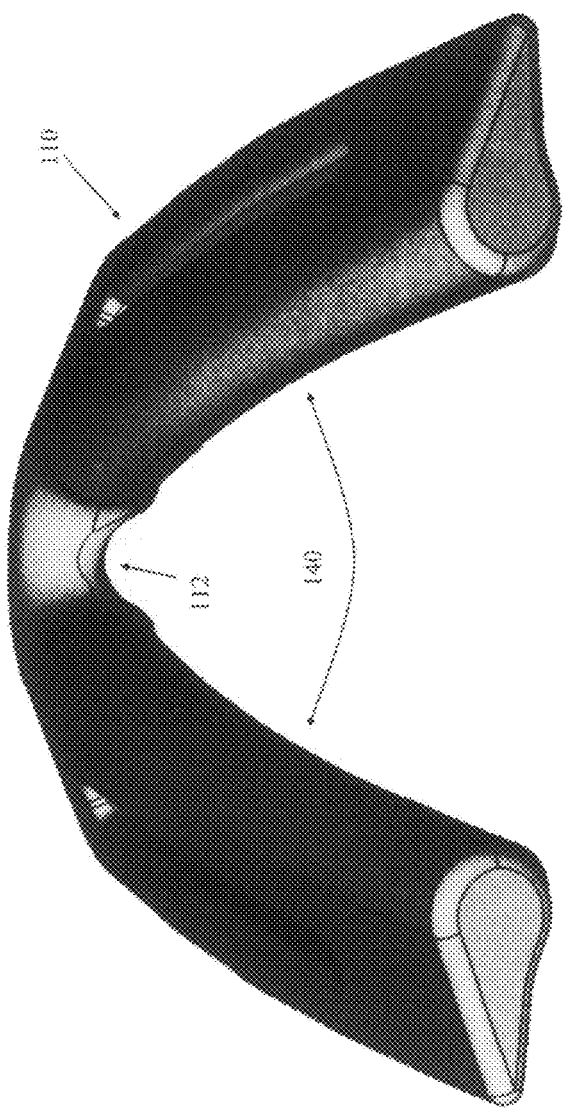

FIGS. 9A-9C illustrate further additional implementations and perspective views of exemplary braces consistent with certain aspects related to the innovations herein. The features of FIGS. 9A and 9B have been set forth above. FIG. 9C illustrates another exemplary implementation of raised portion, rails or ribs 161/162, which may be comprised of such structures that span only a portion of the muscle/tendon-engaging regions, as shown by the raised regions 161, though which can span the full length of such regions, as shown via the dashed regions 162. 2. The protrusions may have a rounded composition that presses down on the injured region/tendons, firmly cradles the injured area, and may prevent unwanted muscle/tendon group flexion. In one implementation, for example, the ribs may be ramped, such as ramped on the legs, protruding towards the rear of the "V." In another exemplary implementation, the ribs may include or be defined by one or more tendon grooves on or along the front of the V, eliminating the belly in the middle of the V. The underside of the V-shaped member may include a anti-slip coating or material, such as a spray-on materials that imparts tackiness to prevent unwanted movement of the member when the user's arm becomes wet or sweaty.

Further, in the "V"-shaped implementations, the size of the "V", angle of the "V" and the length of the "V" legs can be of varying dimensions. For example, the base or bottom portion of the "V" (where the leg segments join) may be constructed of thicker material to a different (higher) differential of force on the region of the compressed muscle/tendons located towards the user's hand.

FIGS. 10A-10C are illustrations of another exemplary device consistent with certain aspects related to the innovations herein. Specifically, FIGS. 10A-10C illustrate a dual- or combination device that includes two of the brace elements set forth above incorporated together via one strap. A first brace element is positioned on the exterior region of the arm, as shown in FIG. 7B, while a second brace element is positioned on an interior region of the arm, as shown in FIG. 8B.

Furthermore, the innovations herein may also include methods and methods of doing business consistent with the above disclosure. For example, a method of providing supplemental support to an arm of a user is provided, the method comprising applying a brace according to the above disclosure to the arm of the user. Further, methods of doing business are also provided. For example, an exemplary method of doing business may comprise implementing a website offering the brace according to the above disclosure for sale, communicating over a network regarding effecting a delivery of the brace, and processing financial information regarding receipt of consideration in connection with or relation to the brace being offered for sale on the website.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

Other embodiments of the invention will be apparent to those skilled in the art from consideration of the specification and practice of the invention disclosed herein. It is intended that the specification and examples be considered as exemplary only, with a true scope and spirit of the invention being indicated by the disclosure above in combination with the following paragraphs describing the scope of one or more embodiments of the following invention.

The invention claimed is:

1. A method of doing business comprising:
   implementing a website offering a brace for a user's arm for sale, the brace comprising:
   a rigid element including 2 arm-engaging portions that are fabricated in a fixed, acute, V-shaped angular relationship with respect to each other to form a rigid jaw therebetween;
   a strap comprising elastic material attachable to the element and configured to encircle the arm; and
   raised portions, rails or ribs positioned along the muscle/tendon-engaging regions on inner sides of the V arms towards the inner, open edge;
   wherein the arm-engaging portions include muscle/tendon-engaging regions have leading face/edges positioned inwardly, in a direction towards/facing the strap into an area encircled by the strap, such that the regions are positioned to engage one or more muscles and/or tendons of the user's arm along the leading face/edge;
   wherein a first leading face/edge corresponding to a first muscle/tendon-engaging region is positioned in an angularly displaced relationship with a second leading face/edge corresponding to a second muscle/tendon-engaging region; and
   wherein the first leading face/edge is angularly displaced between about 22 degrees and about 45 degrees from the second leading face/edge;
   wherein the strap of elastic material, together with the rigid element, form a loop shaped to encircle the user's arm and flexibly bias the rigid element towards the strap with first and second legs of the rigid jaw being biased by the strap inwardly in a V-shaped configuration with respect to each other such that the first and second legs extend inward into the loop in a position to engage and apply force to objects within the loop via V-shaped element structure given by inner angular edges of the first and second legs, which are positioned in acute relationship with respect to each other to guide and gather muscles/tendons within the loop biased by the elastic strap into the rigid jaw;
   communicating over a network regarding effecting a delivery of the brace; and
   processing financial information regarding receipt of consideration in connection with or relation to the brace being offered for sale on the website.

2. The method of claim 1 wherein the rigid element is shaped to conform to a user's arm in having a first curvature, as measured along a top side view perspective, characterized as having a rise (height) of about 3 mm to about 4 mm, along a run (length) of about 4 cm.

3. The method of claim 2 wherein the curvature is measured across the full length of a largest cross-section characterized by a largest range of the run (length) of the rigid member that engages the user.

4. The method of claim 1 wherein the constraining force is characterized by restriction of muscles/tendons in a flexible, non-rigid manner.

5. The method of claim 1 wherein the rigid element is shaped to conform to a user's arm in having a first curvature, as measured along a side view perspective, characterized as having a rise of about 1 mm to about 8 mm, along a run (length) of about 5 to about 9 cm.

6. The method of claim 1 wherein the rigid element is shaped to conform to a user's arm in having a first curvature, as measured along a side view perspective, characterized as having a rise (height) of about 2 mm to about 6 mm, along a run (length) of about 6 to about 8 cm.

7. The method of claim 1 wherein the rigid element is shaped to conform to a user's arm in having a first curvature, as measured along a side view perspective, characterized as having a rise of about 3 mm to about 4 mm, along a run (length) of about 7 cm.

8. The method of claim 1 wherein the rigid element is shaped to conform to a user's arm in having a first curvature, as measured along a top side view perspective, characterized as having a rise of between about 1 mm and about 6 mm along a run (length) of about 2 to about 6 cm.

9. The method of claim 1 wherein the rigid element is shaped to conform to a user's arm in having a first curvature, as measured along a top side view perspective, characterized as having a rise (height) of about 2 mm to about 5 mm, along a run (length) of about 3 to about 5 cm.

10. The method of claim 1 further comprising raised portions, rails or ribs along the muscle/tendon-engaging regions, wherein the raised portions, rails or ribs are about 3 mm to about 7 mm in width and about 1 mm to about 4 mm in height, or are about 5 mm in width and about 2 mm to about 3 mm in height.

11. The method of claim 1 wherein the brace is about 1.5 inches to about 2.25 inches in length and about 1.25 inches to about 2 inches across the greatest width.

12. The method of claim 1 wherein the brace is about 2 inches to about 3 inches in length and about 1.75 inches to about 3 inches across the greatest width.

* * * * *